(12) United States Patent
Waddington et al.

(10) Patent No.: US 11,515,011 B2
(45) Date of Patent: Nov. 29, 2022

(54) K-MER BASED GENOMIC REFERENCE DATA COMPRESSION

(71) Applicant: International Business Machines Corporation, Armonk, NY (US)

(72) Inventors: Daniel Waddington, Morgan Hill, CA (US); Mark Kunitomi, San Francisco, CA (US); Amir Abboud, Sunnyvale, CA (US); Samyukta Satish Rao, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 630 days.

(21) Appl. No.: 16/537,184

(22) Filed: Aug. 9, 2019

(65) Prior Publication Data

US 2021/0043282 A1    Feb. 11, 2021

(51) Int. Cl.
*G06F 17/00*    (2019.01)
*G06F 7/00*     (2006.01)
(Continued)

(52) U.S. Cl.
CPC .............. *G16B 50/50* (2019.02); *G06F 7/14* (2013.01); *G06F 16/2246* (2019.01); *G16B 30/00* (2019.02); *H03M 7/70* (2013.01)

(58) Field of Classification Search
CPC ..... G16B 50/50; G16B 30/00; G06F 16/2246; G06F 7/14; H03M 7/70
(Continued)

(56) References Cited

U.S. PATENT DOCUMENTS 9,929,746 B2    3/2018  Cox et al.
2004/0059721 A1*  3/2004  Patzer .................... G16B 30/10
(Continued)

FOREIGN PATENT DOCUMENTS

CN    102081707 A    6/2011
CN    106021985 A    10/2016
(Continued)

OTHER PUBLICATIONS

Solomon et al., "Fast search of thousands of short-read sequencing experiments," Nature Biotechnology, vol. 34, No. 3, Mar. 2016, pp. 300-302.
(Continued)

*Primary Examiner* — Pavan Mamillapalli
(74) *Attorney, Agent, or Firm* — Zilka-Kotab, P.C.

(57) ABSTRACT

A computer-implemented method includes receiving genomic data associated with a plurality of genomes and identifying k-mer sets within the genomic data. The method includes constructing a k-mer subset tree according to the following process: performing iterative pairwise comparisons on the k-mer sets, wherein the iterative pairwise comparisons identify fragments with the most shared k-mers, merging the identified fragments into non-leaf nodes of the k-mer subset tree, and placing each remaining k-mer into a leaf node of the k-mer subset tree. The method includes storing the k-mer subset tree. A computer program product for data compression includes a computer readable storage medium having program instructions embodied therewith. The program instructions are executable by a computer to cause the compute to perform the foregoing method. A system includes a processor and logic. The logic is configured to perform the foregoing method.

18 Claims, 6 Drawing Sheets

(51) Int. Cl.
*G16B 50/50* (2019.01)
*G06F 16/22* (2019.01)
*G16B 30/00* (2019.01)
*H03M 7/30* (2006.01)
*G06F 7/14* (2006.01)

(58) Field of Classification Search
USPC .......................................................... 707/693
See application file for complete search history.

(56) References Cited

U.S. PATENT DOCUMENTS

| | | | |
|---|---|---|---|
| 2009/0024555 A1* | 1/2009 | Rieck | G16B 40/20 706/54 |
| 2009/0150084 A1* | 6/2009 | Colwell | G16B 50/30 702/20 |
| 2011/0257889 A1* | 10/2011 | Klammer | G16B 30/00 702/19 |
| 2012/0330567 A1* | 12/2012 | Bauer | G16B 30/00 702/20 |
| 2013/0031092 A1 | 1/2013 | Bhola et al. | |
| 2014/0214780 A1 | 7/2014 | Lange et al. | |
| 2015/0057947 A1 | 2/2015 | Drmanac et al. | |
| 2015/0169823 A1* | 6/2015 | Chin | G16B 5/00 702/20 |
| 2015/0169824 A1* | 6/2015 | Kermani | G16B 30/10 702/19 |
| 2015/0286775 A1* | 10/2015 | Chin | G16B 30/20 702/20 |
| 2015/0294065 A1* | 10/2015 | Gautier | G16B 50/30 702/19 |
| 2015/0347088 A1* | 12/2015 | Bruestle | G06F 16/2282 707/753 |
| 2015/0347676 A1* | 12/2015 | Zhao | C12Q 1/6869 702/20 |
| 2016/0259880 A1 | 9/2016 | Semenyuk | |
| 2016/0344849 A1* | 11/2016 | Thomas | G16B 30/20 |
| 2017/0096703 A1* | 4/2017 | Dolan | G16B 40/00 |
| 2017/0219557 A1 | 8/2017 | Reid et al. | |
| 2018/0039730 A1* | 2/2018 | Browning | G16B 20/20 |
| 2018/0060484 A1* | 3/2018 | Chin | G06F 16/9024 |

FOREIGN PATENT DOCUMENTS

| | | |
|---|---|---|
| CN | 106295250 A | 1/2017 |
| CN | 106971088 A | 7/2017 |
| CN | 104951672 B | 8/2017 |
| WO | 2015081754 A1 | 6/2015 |
| WO | 2018080477 A1 | 5/2018 |

OTHER PUBLICATIONS

Kingsford et al., "Reference-based compression of short-read sequences using path encoding," Bioinformatics, vol. 31, No. 12, 2015, pp. 1920-1928.

Benoit et al., "De Novo NGS Data Compression," Algorithms for Next-Generation Sequencing Data, Dec. 8, 2017, pp. 1-25.

Wikipedia, "Jaccard index," Wikipedia, Apr. 1, 2019, 7 pages, retrieved from https://en.wikipedia.org/wiki/Jaccard_index.

NCBI, "Welcome to NCBI" National Center for Biotechnology Information, 2019, 1 page, retrieved from https://www.ncbi.nlm.nih.gov/.

Starchenko et al., "Taxonomy name/id Status Report Page," National Center for Biotechnology Information, accessed on Jun. 27, 2019, 2 pages, retrieved from https://www.ncbi.nlm.nih.gov/Taxonomy/TaxIdentifier/tax_identifier.cgi.

NCBI, "The NCBI Taxonomy Homepage," National Center for Biotechnology Information, accessed on Jun. 27, 2019, 1 page, retrieved from https://www.ncbi.nlm.nih.gov/Taxonomy/taxonomyhome.html/index.cgi.

Buckingham et al., "Protein database search using compressed k-mer vocabularies," 23rd Australasian Document Computing Symposium (ADCS '18), Dec. 11-12, 2018, 7 pages.

* cited by examiner

K-MER BASED GENOMIC REFERENCE DATA COMPRESSION

BACKGROUND

The present invention relates to data compression, and more specifically, this invention relates to data compression of k-mer based genomic reference data.

SUMMARY

A computer-implemented method, according to one embodiment, includes receiving genomic data associated with a plurality of genomes and identifying k-mer sets within the genomic data. The method includes constructing a k-mer subset tree according to the following process: performing iterative pairwise comparisons on the k-mer sets, wherein the iterative pairwise comparisons identify fragments with the most shared k-mers, merging the identified fragments into non-leaf nodes of the k-mer subset tree, and placing each remaining k-mer into a leaf node of the k-mer subset tree. The method includes storing the k-mer subset tree.

A computer program product for data compression, according to one embodiment, includes a computer readable storage medium having program instructions embodied therewith. The program instructions are executable by a computer to cause the compute to perform the foregoing method.

A system, according to one embodiment, includes a processor and logic integrated with the processor, executable by the processor, or integrated with and executable by the processor. The logic is configured to perform the foregoing method.

Other aspects and embodiments of the present invention will become apparent from the following detailed description, which, when taken in conjunction with the drawings, illustrate by way of example the principles of the invention.

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The following description discloses several preferred embodiments of systems, methods and computer program products for data compression of K-mer based genomic reference data.

In one general embodiment, a computer-implemented method includes receiving genomic data associated with a plurality of genomes and identifying k-mer sets within the genomic data. The method includes constructing a k-mer subset tree according to the following process: performing iterative pairwise comparisons on the k-mer sets, wherein the iterative pairwise comparisons identify fragments with the most shared k-mers, merging the identified fragments into non-leaf nodes of the k-mer subset tree, and placing each remaining k-mer into a leaf node of the k-mer subset tree. The method includes storing the k-mer subset tree.

In another general embodiment, a computer program product for data compression includes a computer readable storage medium having program instructions embodied therewith. The program instructions are executable by a computer to cause the compute to perform the foregoing method.

In another general embodiment, a system includes a processor and logic integrated with the processor, executable by the processor, or integrated with and executable by the processor. The logic is configured to perform the foregoing method.

Figure 1:
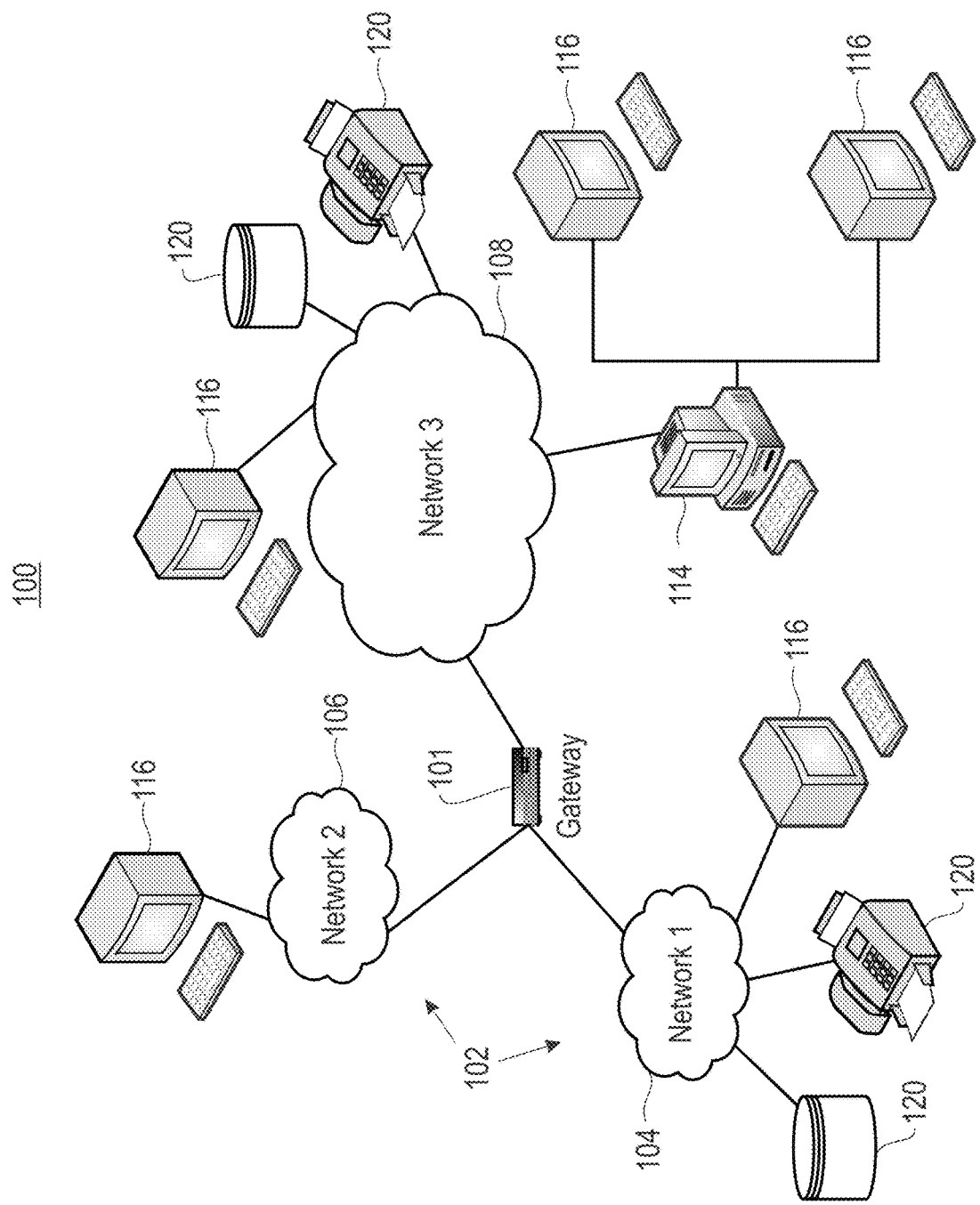
FIG. 1 illustrates a network architecture, in accordance with one embodiment of the present invention.

FIG. 1 illustrates an architecture 100, in accordance with one embodiment. As shown in FIG. 1, a plurality of remote networks 102 are provided including a first remote network 104 and a second remote network 106. A gateway 101 may be coupled between the remote networks 102 and a proximate network 108. In the context of the present architecture 100, the networks 104, 106 may each take any form including, but not limited to a local area network (LAN), a wide area network (WAN) such as the Internet, public switched telephone network (PSTN), internal telephone network, etc.

In use, the gateway 101 serves as an entrance point from the remote networks 102 to the proximate network 108. As such, the gateway 101 may function as a router, which is capable of directing a given packet of data that arrives at the gateway 101, and a switch, which furnishes the actual path in and out of the gateway 101 for a given packet.

Further included is at least one data server 114 coupled to the proximate network 108, and which is accessible from the remote networks 102 via the gateway 101. It should be noted that the data server(s) 114 may include any type of computing device/groupware. Coupled to each data server 114 is a plurality of user devices 116. User devices 116 may also be connected directly through one of the networks 104, 106, 108. Such user devices 116 may include a desktop computer, lap-top computer, hand-held computer, printer or any other type of logic. It should be noted that a user device 111 may also be directly coupled to any of the networks, in one embodiment.

A peripheral 120 or series of peripherals 120, e.g., facsimile machines, printers, networked and/or local storage units or systems, etc., may be coupled to one or more of the networks 104, 106, 108. It should be noted that databases and/or additional components may be utilized with, or integrated into, any type of network element coupled to the networks 104, 106, 108. In the context of the present description, a network element may refer to any component of a network.

According to some approaches, methods and systems described herein may be implemented with and/or on virtual systems and/or systems which emulate one or more other systems, such as a UNIX® system which emulates an IBM® z/OS® environment, a UNIX® system which virtually hosts a Microsoft® Windows® environment, a Microsoft® Windows® system which emulates an IBM® z/OS® environment, etc. This virtualization and/or emulation may be enhanced through the use of VMware® software, in some embodiments.

In more approaches, one or more networks 104, 106, 108, may represent a cluster of systems commonly referred to as a "cloud." In cloud computing, shared resources, such as processing power, peripherals, software, data, servers, etc., are provided to any system in the cloud in an on-demand relationship, thereby allowing access and distribution of services across many computing systems. Cloud computing typically involves an Internet connection between the systems operating in the cloud, but other techniques of connecting the systems may also be used.

Figure 2:
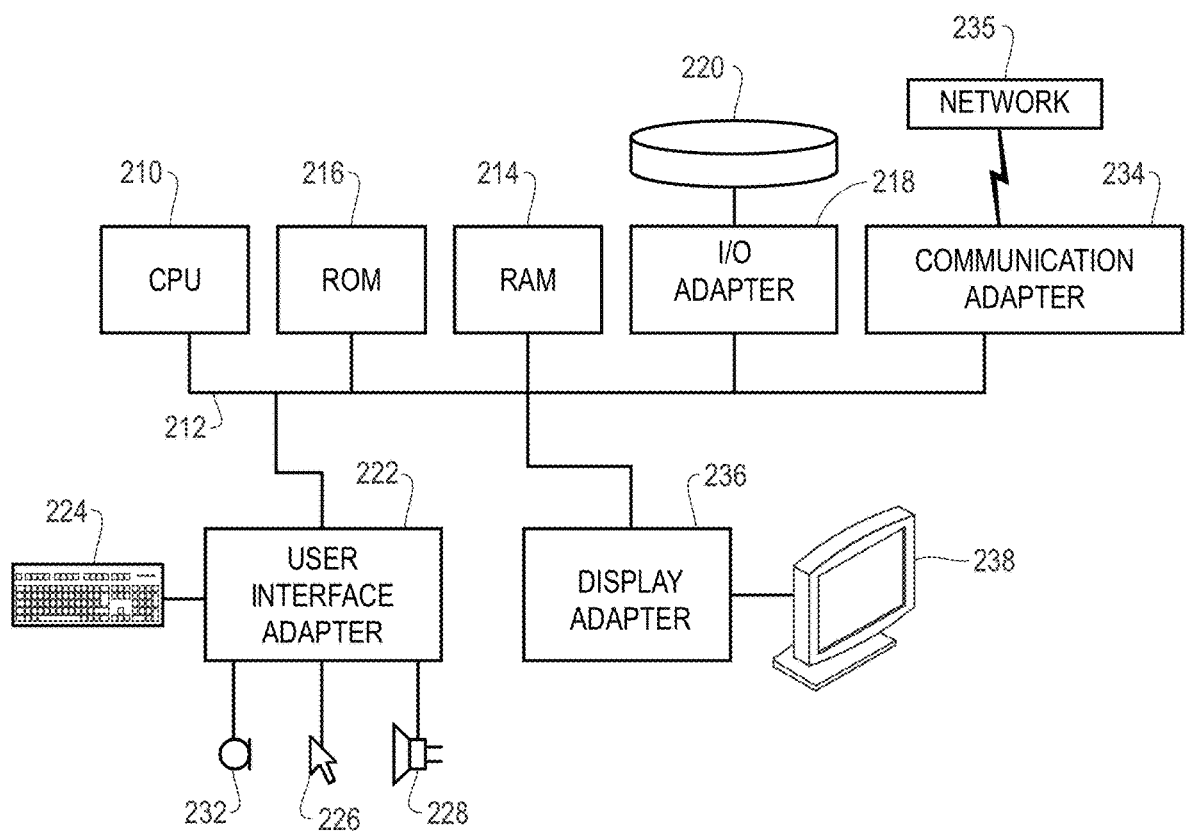
FIG. 2 shows a representative hardware environment that may be associated with the servers and/or clients of FIG. 1, in accordance with one embodiment of the present invention.

FIG. 2 shows a representative hardware environment associated with a user device 116 and/or server 114 of FIG. 1, in accordance with one embodiment. Such figure illustrates a typical hardware configuration of a workstation having a central processing unit 210, such as a microprocessor, and a number of other units interconnected via a system bus 212.

The workstation shown in FIG. 2 includes a Random Access Memory (RAM) 214, Read Only Memory (ROM) 216, an input/output (I/O) adapter 218 for connecting peripheral devices such as disk storage units 220 to the bus 212, a user interface adapter 222 for connecting a keyboard 224, a mouse 226, a speaker 228, a microphone 232, and/or other user interface devices such as a touch screen and a digital camera (not shown) to the bus 212, communication adapter 234 for connecting the workstation to a communication network 235 (e.g., a data processing network) and a display adapter 236 for connecting the bus 212 to a display device 238.

The workstation may have resident thereon an operating system such as the Microsoft® Windows® Operating System (OS), a macOS®, a UNIX® OS, etc. It will be appreciated that a preferred embodiment may also be implemented on platforms and operating systems other than those mentioned. A preferred embodiment may be written using eXtensible Markup Language (XML), C, and/or C++ language, or other programming languages, along with an object oriented programming methodology. Object oriented programming (OOP), which has become increasingly used to develop complex applications, may be used.

Figure 3:
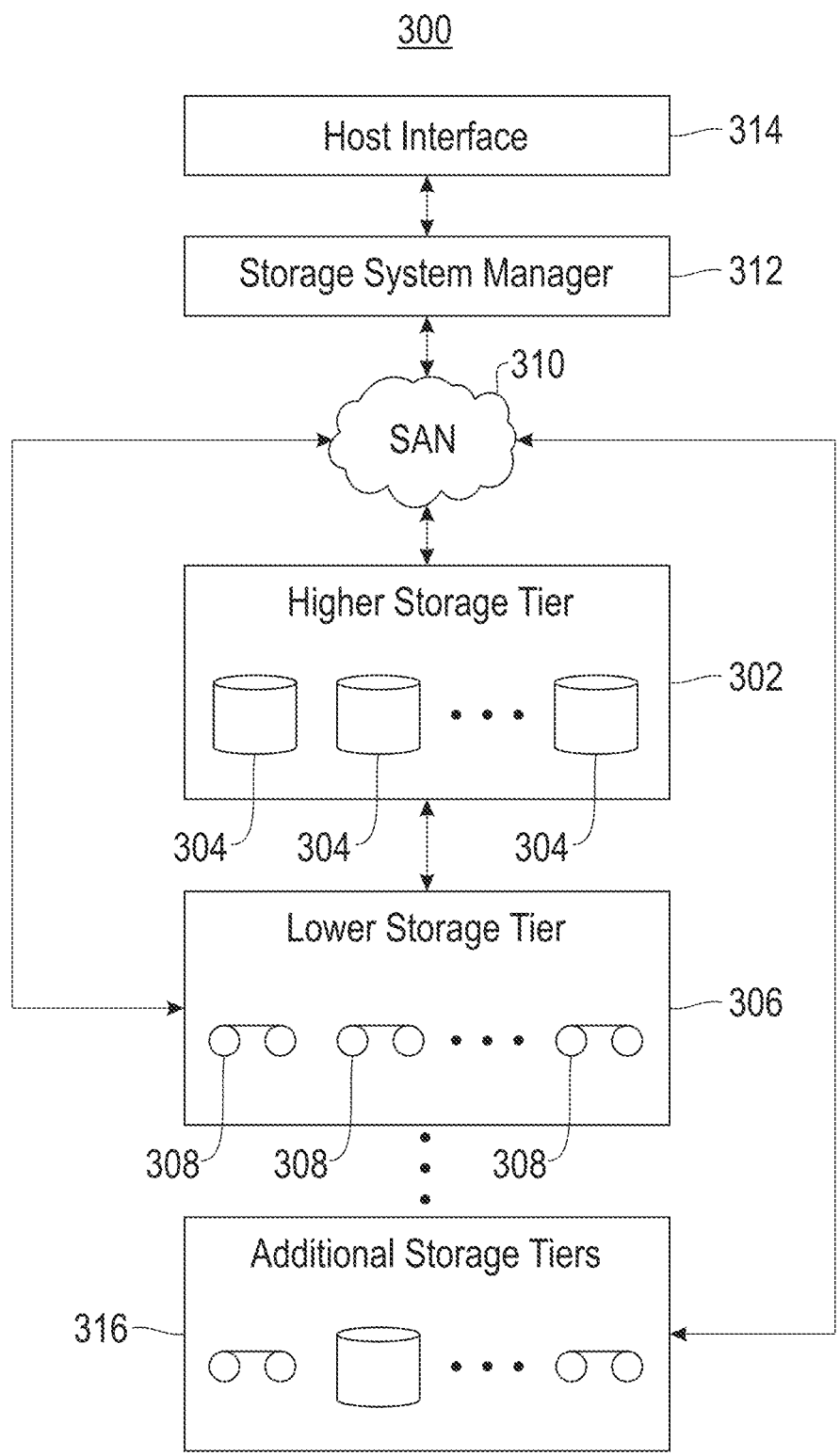
FIG. 3 illustrates a tiered data storage system in accordance with one embodiment of the present invention.

Now referring to FIG. 3, a storage system 300 is shown according to one embodiment. Note that some of the elements shown in FIG. 3 may be implemented as hardware and/or software, according to various embodiments. The storage system 300 may include a storage system manager 312 for communicating with a plurality of media and/or drives on at least one higher storage tier 302 and at least one lower storage tier 306. The higher storage tier(s) 302 preferably may include one or more random access and/or direct access media 304, such as hard disks in hard disk drives (HDDs), nonvolatile memory (NVM), solid state memory in solid state drives (SSDs), flash memory, SSD arrays, flash memory arrays, etc., and/or others noted herein or known in the art. The lower storage tier(s) 306 may preferably include one or more lower performing storage media 308, including sequential access media such as magnetic tape in tape drives and/or optical media, slower accessing HDDs, slower accessing SSDs, etc., and/or others noted herein or known in the art. One or more additional storage tiers 316 may include any combination of storage memory media as desired by a designer of the system 300. Also, any of the higher storage tiers 302 and/or the lower storage tiers 306 may include some combination of storage devices and/or storage media.

The storage system manager 312 may communicate with the drives and/or storage media 304, 308 on the higher storage tier(s) 302 and lower storage tier(s) 306 through a network 310, such as a storage area network (SAN), as shown in FIG. 3, or some other suitable network type. The storage system manager 312 may also communicate with one or more host systems (not shown) through a host interface 314, which may or may not be a part of the storage system manager 312. The storage system manager 312 and/or any other component of the storage system 300 may be implemented in hardware and/or software, and may make use of a processor (not shown) for executing commands of a type known in the art, such as a central processing unit (CPU), a field programmable gate array (FPGA), an application specific integrated circuit (ASIC), etc. Of course, any arrangement of a storage system may be used, as will be apparent to those of skill in the art upon reading the present description.

In more embodiments, the storage system 300 may include any number of data storage tiers, and may include the same or different storage memory media within each storage tier. For example, each data storage tier may include the same type of storage memory media, such as HDDs, SSDs, sequential access media (tape in tape drives, optical disc in optical disc drives, etc.), direct access media (CD-ROM, DVD-ROM, etc.), or any combination of media storage types. In one such configuration, a higher storage tier 302, may include a majority of SSD storage media for storing data in a higher performing storage environment, and remaining storage tiers, including lower storage tier 306 and additional storage tiers 316 may include any combination of SSDs, HDDs, tape drives, etc., for storing data in a lower performing storage environment. In this way, more frequently accessed data, data having a higher priority, data needing to be accessed more quickly, etc., may be stored to the higher storage tier 302, while data not having one of these attributes may be stored to the additional storage tiers 316, including lower storage tier 306. Of course, one of skill in the art, upon reading the present descriptions, may devise many other combinations of storage media types to implement into different storage schemes, according to the embodiments presented herein.

According to some embodiments, the storage system (such as 300) may include logic configured to receive a request to open a data set, logic configured to determine if the requested data set is stored to a lower storage tier 306 of a tiered data storage system 300 in multiple associated portions, logic configured to move each associated portion of the requested data set to a higher storage tier 302 of the tiered data storage system 300, and logic configured to assemble the requested data set on the higher storage tier 302 of the tiered data storage system 300 from the associated portions.

Of course, this logic may be implemented as a method on any device and/or system or as a computer program product, according to various embodiments.

K-mers are fixed length substrings of length K. In the context of genetic sequences (DNA), k-mers represent substrings of A, C, T, and G nucleotides. "K-mer sets" are unique sets of k-mers that have been extracted from a longer sequence. Conversion of sample sequences into k-mers and then performing analyses on the resulting sets has a number of applications in classification and identification of genetic sequence samples.

Alignment-based sequence analysis arranges the sequences of nucleic acids (e.g., DNA and RNA) to identify regions of similarity that may be indicative of functional, structural, and/or evolutionary relationships between the sequences. K-mer based analysis is considered an alignment-free alternative to alignment-based sequence comparisons. K-mer analysis is particularly scalable and resilient to comparisons between strings with significant edits (e.g., multi-nucleotide insertions and/or deletions). K-mer based approaches are well suited to analysis of bacterial genomes due to this inherent resilience to highly changing, multi-nucleotide mutations.

K-mer analysis may be used in the classification of DNA samples through Polymerase Chain Reaction (PCR) techniques to amplify specific regions of a sample. The k-mer may be used as the amplicon for the PCR reaction.

Bacterial identification may be used to determine whether a sample of bacteria belongs to a given "in-group" and does not belong to a broader "out-group." For example, the in-group may be the serovar *Salmonella* Virchow and the out-group may be the broader species *Salmonella*. The objective of the detection may be to determine the presence *Salmonella* Virchow and to prevent the triggering of a false-positive by some other member of the broader *Salmonella* family.

Computationally, k-mer based analysis involves creating a k-mer set of the intersection of all k-mers in all genomes of the in-group and a union k-mer set of all the k-mers in the out-group. Both sets may be a set of unique k-mers. From these two k-mer sets, the relative complement is performed in order to identify k-mers in the in-group that are not in the out-group. K-mers in the relative complement are the amplicon candidates to be used in the primer design process.

Another example of k-mer based analysis considers sequence "likeness" by measuring similarity of k-mer sets using a distance metric (e.g., the Jaccard index). K-mer based analysis relies on accurately labelled reference data such as reference data attainable from the National Center for Biotechnology Information (NCBI). The majority of reference data is sequenced using short-read sequencing in conjunction with gene assembly (e.g., shotgun sequencing).

Each DNA sequence comprises two forms: forward (e.g., 5' to 3' direction) and the reverse complement. To reduce the cost of k-mer set analyses, k-mers may be stored in "canonical" form, which chooses one of the two directions described above to reduce the workload for analysis of the k-mers. Saving k-mer sets avoids recalculating the canonical form for performing various sliding window techniques on the data. Canonical selection may be any consistent criteria. In an exemplary approach, the canonical form selection may be based on alphanumeric form.

The direction of reference genomes is not always known. K-mer sets are conventionally constructed by applying a sliding window of length K, extracting the canonical form, and then inserting the canonical form into a frequency counted hash table. The production of k-mer sets results in a multiplicative increase in storage requirements as the k-mers represent K*(sequence length−K+1) data, or roughly, K times more data than the original sequence. At high K values (e.g., 100 and above), the production of k-mer sets represents a significant, non-optimal increase in storage requirements.

Conventional analysis of k-mer sets, including sliding window techniques, requires significant overhead. Performing calculations for the various hash tables, redundancy collisions, etc., are expensive. Existing techniques for data compression (e.g., Huffman coding) are compute-costly and only leverage the repetition of symbols.

Bacteria are ever-evolving organisms that modify their DNA sequences through mutation (e.g., caused by environmental conditions) and exchange (e.g., DNA transfer across multiple strains of bacteria). Bacteria have similarity between strains due to the evolutionary process and basic organismic functional needs. Additionally, multiple strains of bacteria share common ancestors, resulting in inherited genetic similarities.

Phylogenetic tree (e.g., evolutionary tree) branching diagrams represent the evolutionary relationships among various biological species and/or other species based on similarities and/or differences in genetic characteristics.

Various embodiments of the present invention describe a method of storing and/or saving k-mer sets for fast recovery and analysis of the sets without reconstruction through a sliding window technique. At least some of the embodiments described herein exploit the inherent phylogenetic relationships across multiple genomes to create a space-efficient (e.g., data compressed) reference repository. The compressed form avoids redundancy by arranging data in a hierarchical tree whereby a given genome G is reconstituted by the "piecemeal combination" of fragments along the corresponding spine (e.g., leaf to root) of the tree. Using various approaches described herein, the saved k-mer sets do not require decompression per se on loading from storage and the fragments are simply combined. At least some of the embodiments disclosed herein improve read/recovery rate for k-mer based iterative analysis including dynamic loading and/or operations performed on the k-mers. In preferred embodiments, there is no information loss (e.g., the data compression is lossless).

Figure 4:
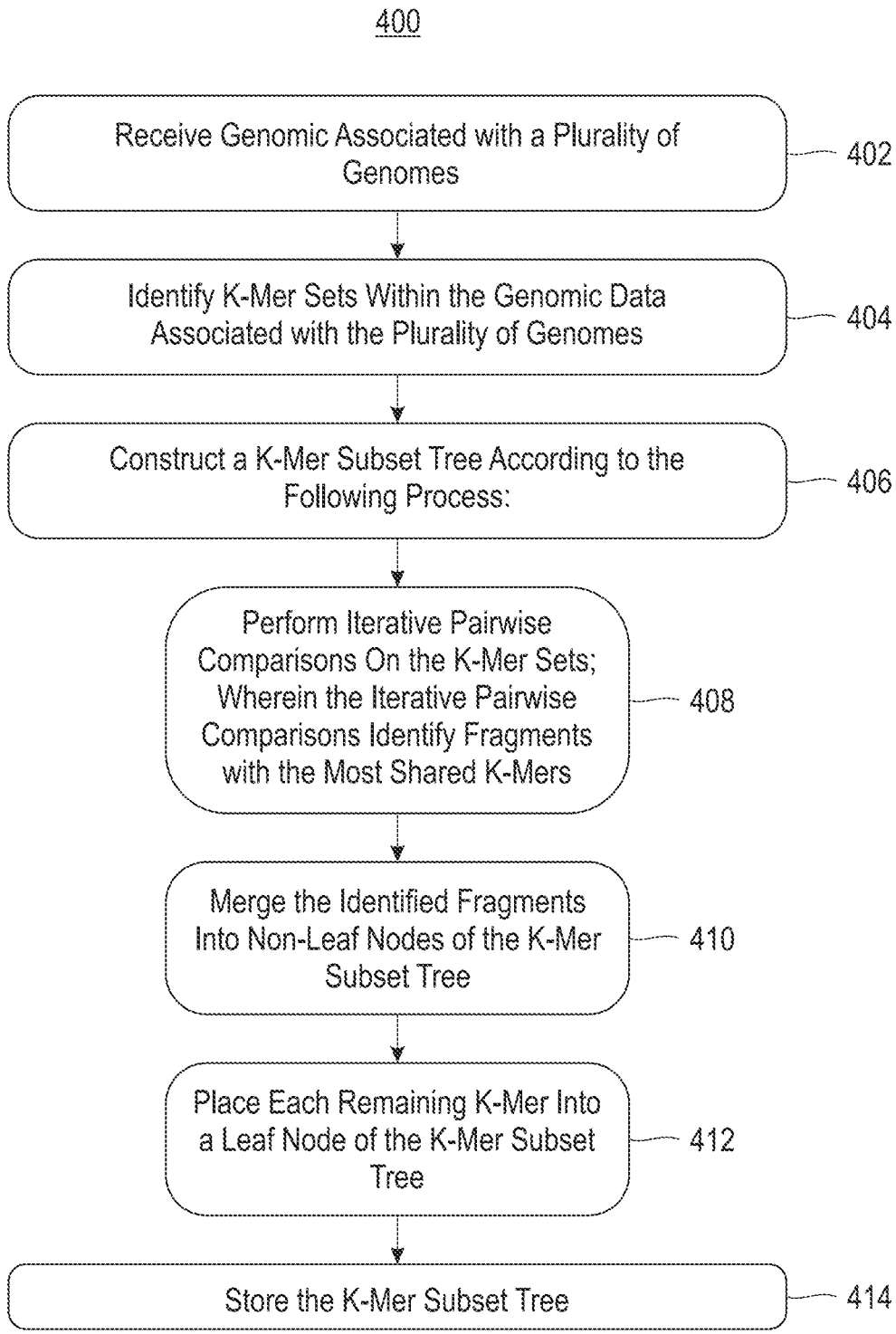
FIG. 4 is a flowchart of a method in accordance with one embodiment of the present invention.

Now referring to FIG. 4, a flowchart of a method 400 is shown according to one embodiment. The method 400 may be performed in accordance with the present invention in any of the environments depicted in FIGS. 1-3 and 5-6, among others, in various embodiments. Of course, more or less operations than those specifically described in FIG. 4 may be included in method 400, as would be understood by one of ordinary skill in the art upon reading the present descriptions.

Each of the steps of the method 400 may be performed by any suitable component of the operating environment. For example, in various embodiments, the method 400 may be partially or entirely performed by computers, or some other device having one or more processors therein. The processor, e.g., processing circuit(s), chip(s), and/or module(s) implemented in hardware and/or software, and preferably having at least one hardware component may be utilized in any device to perform one or more steps of the method 400. Illustrative processors include, but are not limited to, a central processing unit (CPU), an application specific integrated circuit (ASIC), a field programmable gate array (FPGA), etc., combinations thereof, or any other suitable computing device known in the art.

As shown in FIG. 4, method 400 includes operation 402. Operation 402 includes receiving genomic data associated with a plurality of genomes. The genomic data associated with the plurality of genomes may be received in any manner known in the art. In a preferred approach, the genomic data is received as a DNA string sequence of nucleotides for each of the genomes as would be understood by one having ordinary skill in the art.

Operation 404 includes identifying k-mer sets within the genomic data associated with the plurality of genomes. In various embodiments presented herein, a k-mer set refers to a set of k-mers derived from a genome. In a preferred approach, each genome is associated with a unique k-mer set. In a preferred embodiment, the k-mer sets are identified using a single canonical form. A single canonical form is chosen to represent the k-mers to reduce redundancy (e.g., no two k-mers in a k-mer set represent the same sequence of genomic data). A single canonical form reduces the workload. A single canonical form prevents reconstructing all the k-mers in the string. In a preferred approach, the canonical form is based on an alphanumerical form.

In a preferred embodiment, the k-mer set for each of the plurality genomes is identified using a sliding window technique known in the art. For example, a sliding window traverses the string of genomic data to select the canonical form and a hash value is calculated and stored in a hash table for each point in the sliding window. The frequency count for the hash entry in the hash table may be used to detect collisions in the hash values (e.g., redundancy). The frequency count for the hash entry in the hash table may be used to determine the number of genomes to which the k-mer belongs.

In preferred approaches, each k-mer set is unique for each genome and each k-mer within a k-mer set is a fixed length. The fixed length is the same for all k-mers in the set.

Operation 406 includes constructing a k-mer subset tree. In a preferred embodiment, each non-leaf node in the tree is an intersection of all child nodes and each leaf node in the tree is a remainder of the k-mers not present in the union of the parental nodes. Each leaf node in the tree is the relative complement of the original genome k-mer set and the intersection of the non-leaf nodes. Specifically, all nodes of the tree represent a subset of the data. Each leaf node of the tree defines a complete k-mer reference set (e.g., for a single genome or for a group of genomes).

In one approach, the k-mer subset tree is a binary tree. A binary tree may refer to a tree where each node has exactly two children. In other approaches, the k-mer subset tree is a non-binary tree.

In a preferred embodiment, constructing the k-mer subset tree includes the process comprising operations 408-412.

Operation 408 includes performing iterative pairwise comparisons on the k-mer sets, wherein the iterative pairwise comparisons identify fragments with the most shared k-mers. Fragments may refer to subsets of data within the genomic data. Fragments include one or more k-mers that belong to one or more genomes. In one approach, fragments may refer to subsets of k-mers. In a preferred embodiment, the iterative pairwise comparisons on the k-mer sets are based on a similarity measure. The k-mer sets may be used to determine the genome-to-genome distances for the plurality of genomes. For example, for n genomes, the iterative pairwise comparisons comprise n genome comparisons to determine which fragments are closest by comparison. In a preferred approach, the similarity measure for the iterative pairwise comparisons is the Jaccard index.

Operation 410 includes merging the identified fragments into non-leaf nodes of the k-mer subset tree. Fragments may be merged based on the similarity measures described above. In a preferred embodiment, at least two identified fragments may be merged into a non-leaf node. The non-leaf nodes of the k-mer subset tree may comprise the intersection of all k-mers that are common to every child node. In a preferred embodiment, the non-leaf nodes of the k-mer subset tree represent subsets of k-mers that do not exist higher up (e.g., in any parent) in the k-mer subset tree.

In response to merging the identified fragments with the most shared k-mers, the method 400, the iterative pairwise comparisons may be recalculated for the merged non-leaf nodes and all the remaining fragments. The merging and recalculating of iterative pairwise comparisons may be repeated until all overlapping fragments are merged into non-leaf nodes of the k-mer subset tree.

In some approaches, operation 412 includes placing any remaining fragments (e.g., unique k-mers) into leaf nodes of the k-mer subset tree. In a preferred approach, each remaining fragment is placed into a unique leaf node in the k-mer subset tree. In one approach, the leaf nodes comprise k-mers that are unique to the corresponding labelled reference set. In a preferred embodiment, the leaf nodes comprise k-mers which do not exist in any higher ancestor.

Operation 414 includes storing the k-mer subset tree. The k-mer subset tree may be saved in any manner known in the art. The k-mer subset tree may be saved to any storage system known in the art. In a preferred embodiment, the non-leaf nodes and/or leaf nodes of the k-mer subset tree are stored in a table. In a preferred embodiment, each unique k-mer is stored exactly once in the k-mer subset tree.

In a preferred approach, each non-leaf node and each leaf node may be stored as a reference repository for storing k-mer sets for relatively fast recovery. The reference repository allows for analysis of k-mer sets without reconstruction through conventional sliding window techniques. The data efficient form of the reference repository reduces redundancy/repetition by arranging data in a hierarchical tree.

In preferred embodiments, in response to receiving a request for genomic data, at least one genome may be reconstituted from the single corresponding leaf node and the ascending non-leaf nodes in the spine of the k-mer subset tree. In various approaches, reconstituting the one or more genomes refers to reconstructing a k-mer set using the fragments merged into the non-leaf nodes along the spine of the k-mer subset tree and k-mers in a corresponding leaf node. It should be understood by one having ordinary skill in the art that any non-leaf node and/or leaf node may be reconstituted using the non-leaf nodes of the spine of the k-mer subset tree.

In one approach, reconstituting one or more genomes may comprise the union of the non-leaf nodes of the spine of the k-mer subset tree and a corresponding leaf node. In a preferred embodiment, genomes may be reconstituted by the combination of fragments along the corresponding spine (e.g., leaf to root) of the tree without decompression on loading from storage.

Various embodiments of the present invention may include operations for constructing a k-mer subset tree a priori (e.g., based on reference data). In an alternative embodiment, the k-mer subset tree may be constructed based on a known taxonomic tree and/or a known phylogenetic reference tree.

In various approaches, new genomic data (e.g., corresponding to new genomes) may be added to the k-mer subset tree after the construction and/or storage of the k-mer subset tree. A k-mer subset tree comprising new genomic data may be used to reconstitute genomic data according to the various operations disclosed herein.

In various embodiments, at least some of the operations of method 400 may be used with existing dictionary-based compression techniques applied at a per-fragment basis. Such compression may require decompression during the set reconstruction as would be understood by one having ordinary skill in the art upon reading the present disclosure. Other embodiments may include employing cluster-analysis techniques to determine what fragments to merge within the k-mer subset tree.

In one approach, the k-mers may be stored in contiguous regions for reconstruction of a region using a De Bruijn graph. Symbolic encoding may be applied for additional reduction in the data footprint as would be understood by one having ordinary skill in the art upon reading the present disclosure.

Figure 5:
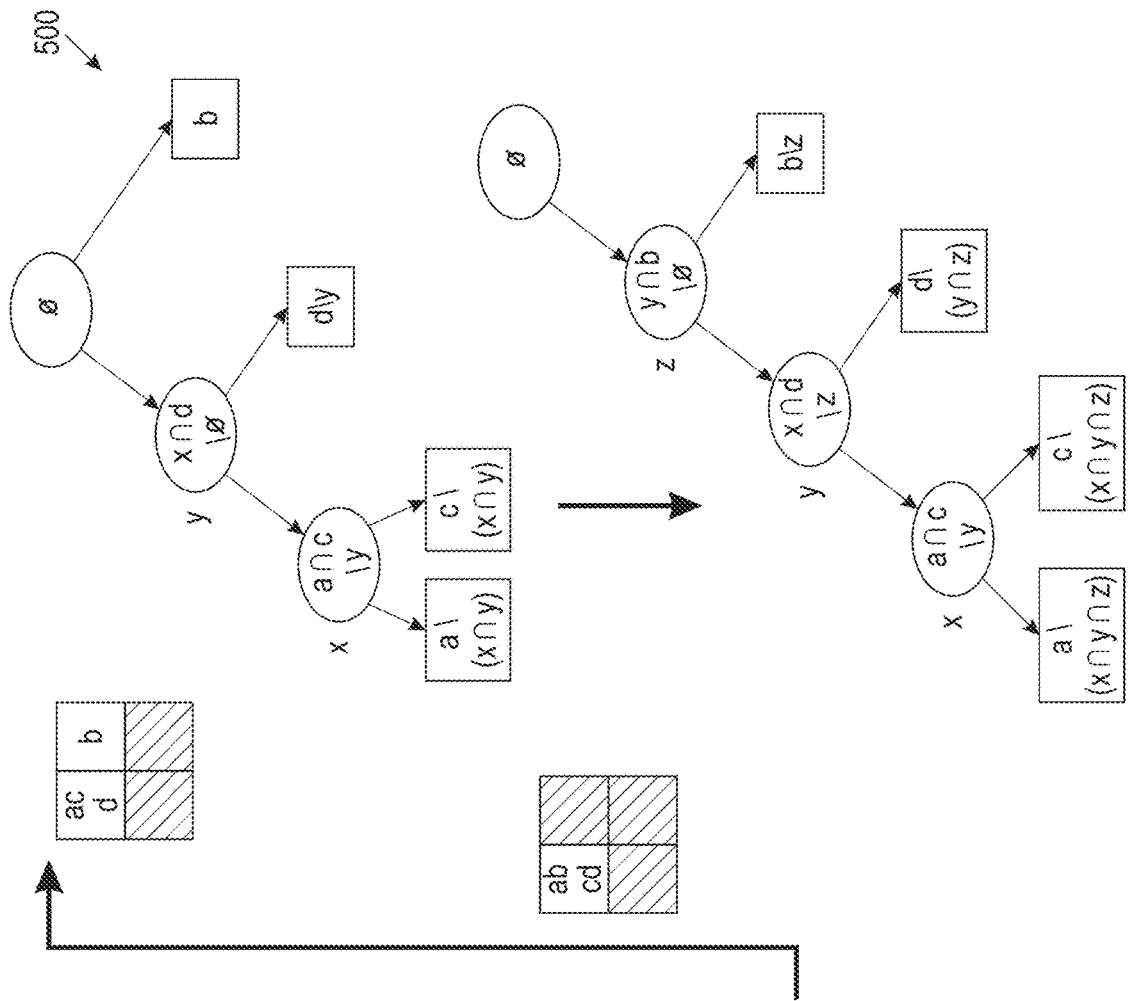
FIG. 5 is an exemplary implementation of the method of FIG. 4 in accordance with one embodiment of the present invention.
Figure 5:
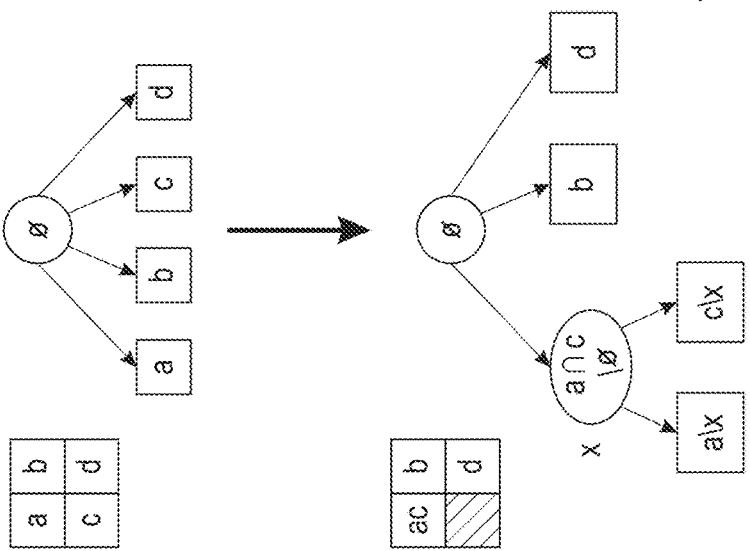

Now referring to FIG. 5, an exemplary implementation 500 of method 400 is shown according to one embodiment. The implementation 500 may be performed in accordance with the present invention in any of the environments depicted in FIGS. 1-4 and 6, among others, in various embodiments. Of course, more or less operations than those specifically described in FIG. 5 may be included in the implementation 500 of method 400, as would be understood by one of ordinary skill in the art upon reading the present descriptions.

Each of the steps of the implementation 500 may be performed by any suitable component of the operating environment. For example, in various embodiments, the implementation 500 may be partially or entirely performed by computers, or some other device having one or more processors therein. The processor, e.g., processing circuit(s), chip(s), and/or module(s) implemented in hardware and/or software, and preferably having at least one hardware component may be utilized in any device to perform one or more steps of the implementation 500. Illustrative processors include, but are not limited to, a central processing unit (CPU), an application specific integrated circuit (ASIC), a field programmable gate array (FPGA), etc., combinations thereof, or any other suitable computing device known in the art.

Implementation 500 includes fragments a, b, c, d. At each iterative pairwise comparison in implementation 500, two fragments with the most shared k-mers are merged into non-leaf nodes of a k-mer subset tree. The choice of which fragments to merge is based on a similarity measure between the fragments.

For each iterative pairwise comparison, the two most similar fragments (e.g., in the first comparison, a and c) are merged. In one embodiment, the fragments are merged based on a pairwise similarity calculation. For example, the pairwise calculations for the initial comparisons include comparing a-b, a-c, a-d, b-c, and c-d. Fragments a and c are merged in the tree by creating a new set x, which defines the intersection of a and c. The two remaining fragment children are a\x and c\x, which define the relative complements of x in a and x in c, respectively. In a preferred embodiment, a may be reconstituted as x∪(a\x). In another embodiment, a may be reconstituted as (a∩c)∪(a\(a∩c)). Any merged fragments are removed from future pairwise comparisons. The leaf nodes become the remainder k-mers (e.g., the relative complements).

The next iterative pairwise comparison compares the remaining fragments and the new set (e.g., new set x compared to b, and, new set x compared to d). Fragment d has the most shared k-mers with the new set x. Fragments d and x are merged into a new non-leaf node y.

The next comparison compares the new set y and the remaining fragment b. Fragments y and b are merged into a new non-leaf node z. The new leaf node (e.g., b\z) comprises any remaining, unique k-mers.

The iterative pairwise comparisons may be performed to determine the similarity between the new merged set and the remaining fragments in the tree. In a preferred approach, the iterative pairwise comparisons are performed until all the fragments are combined. In this exemplary implementation 500, a may be reconstituted as (a\(x∩y∩z))∪x∪y∪z. In a preferred embodiment, each non-leaf node is an intersection and each leaf node is a remaining fragment (e.g., in some approaches these are the remaining, unique k-mers).

Figure 6:
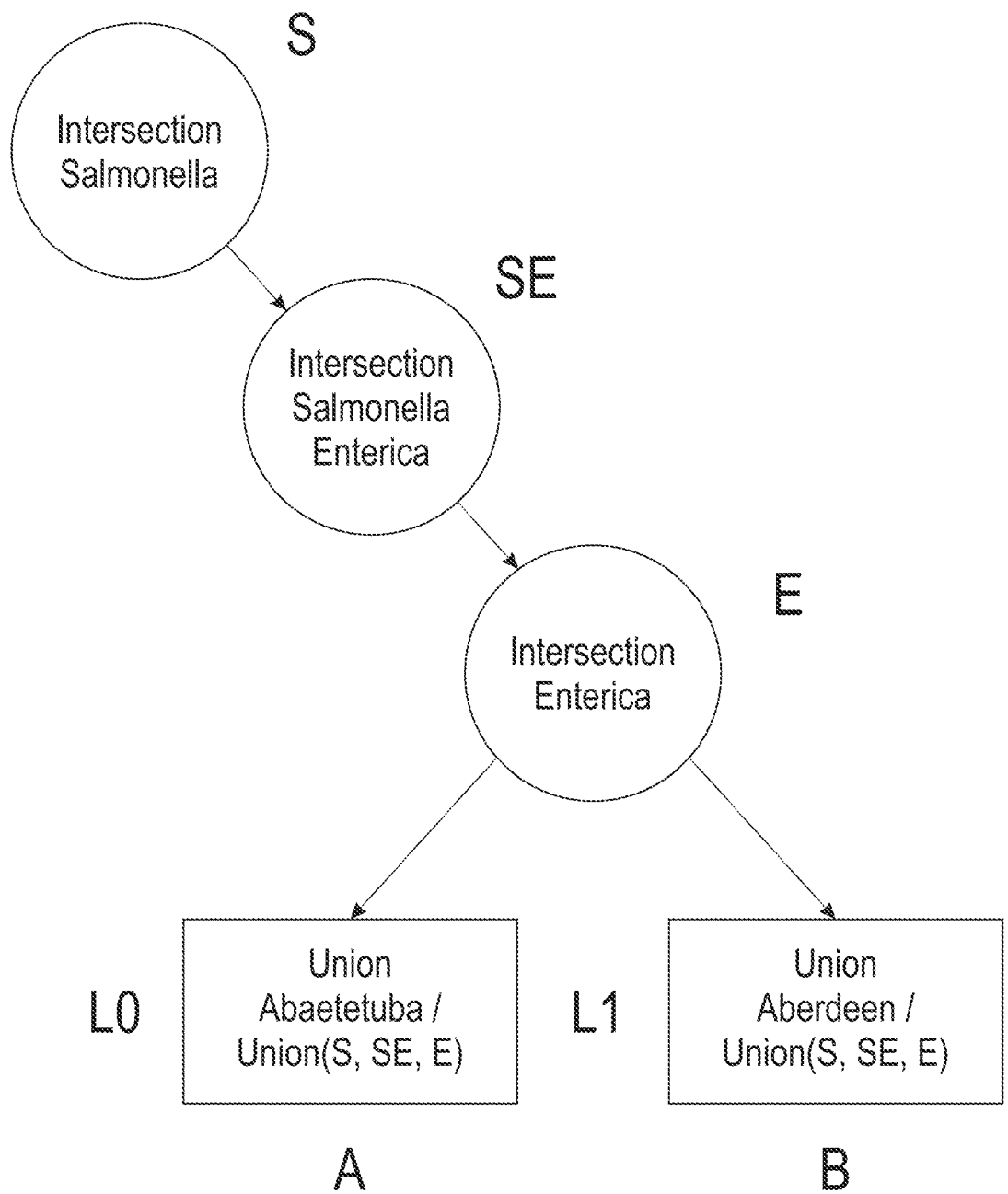
FIG. 6 is an exemplary output of the method of FIG. 4 in accordance with one embodiment of the present invention.

FIG. 6 depicts an exemplary output 600 of method 400, in accordance with one embodiment. As an option, the present output 600 may be implemented in conjunction with features from any other embodiment listed herein, such as those described with reference to the other FIGS. Of course, however, such an output 600 and others presented herein may be used in various applications and/or in permutations which may or may not be specifically described in the illustrative embodiments listed herein. Further, the output 600 presented herein may be used in any desired environment.

The exemplary output 600 depicts a k-mer set tree wherein each non-leaf node is an intersection of k-mers and each leaf node is a remainder of the k-mers not present in the union of the parental nodes. Each leaf node is the relative complement of the original genome k-mer set and the intersection of the non-leaf nodes. To reconstitute genomes A and/or B, the fragments from the spine of the tree (e.g., S, SE, E) and the corresponding leaf nodes (e.g., L0, L1, respectively) may be combined.

In a preferred embodiment, as shown in FIG. 6, non-leaf nodes represent sets of k-mers that do not exist higher up in an ancestor. For example, set SE does not contain any k-mers that are present in set S. Set E does not contain any k-mers that are present in set SE. The k-mers in S belong to all non-leaf nodes and both genomes. Each k-mer is stored in the k-mer subset tree exactly once in this exemplary output 600. Non-leaf nodes represent the intersection of all k-mers that are common to every child below the non-leaf node in the tree. For example, k-mers in non-leaf node E are present in both genome A and genome B. Any k-mers that belong to both set SE and set E are represented only once in set SE. Similarly, k-mers common to set S and SE are represented in the higher non-leaf node set S.

In a preferred embodiment, as shown in FIG. 6, k-mers belonging to the leaf nodes of the tree are unique to the corresponding labelled references set and do not exist in any higher ancestor (e.g., non-leaf node). In a preferred approach, the k-mers are unique (e.g., a k-mer of B belongs to exactly one group of S, SE, E, and L1).

In preferred embodiments, in response to receiving a request for genomic data, at least one genome may be reconstituted from the spine of the k-mer subset tree and a corresponding leaf node. In various approaches, reconstituting the one or more genomes refers to reconstructing a genome using the k-mer sets merged into the non-leaf nodes along the spine of the k-mer subset tree. It should be understood by one having ordinary skill in the art that any non-leaf node and/or leaf node may be reconstituted using the spine of the k-mer subset tree. Reconstituting a genome may include the union of the non-leaf nodes of the spine of the k-mer subset tree and a corresponding leaf node. In a preferred embodiment, genomes may be reconstituted by the combination of fragments along the corresponding spine (e.g., leaf to root) of the tree without decompression on loading from storage. According to output 600, A may be reconstituted as A=L0UEUSEUS. B may be reconstituted as B=L1UEUSEUS.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Moreover, a system according to various embodiments may include a processor and logic integrated with and/or executable by the processor, the logic being configured to perform one or more of the process steps recited herein. The processor may be of any configuration as described herein, such as a discrete processor or a processing circuit that includes many components such as processing hardware, memory, I/O interfaces, etc. By integrated with, what is meant is that the processor has logic embedded therewith as hardware logic, such as an application specific integrated circuit (ASIC), a FPGA, etc. By executable by the processor, what is meant is that the logic is hardware logic; software logic such as firmware, part of an operating system, part of an application program; etc., or some combination of hardware and software logic that is accessible by the processor and configured to cause the processor to perform some functionality upon execution by the processor. Software logic may be stored on local and/or remote memory of any memory type, as known in the art. Any processor known in the art may be used, such as a software processor module and/or a hardware processor such as an ASIC, a FPGA, a central processing unit (CPU), an integrated circuit (IC), a graphics processing unit (GPU), etc.

It will be clear that the various features of the foregoing systems and/or methodologies may be combined in any way, creating a plurality of combinations from the descriptions presented above.

It will be further appreciated that embodiments of the present invention may be provided in the form of a service deployed on behalf of a customer to offer service on demand.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
   receiving genomic data associated with a plurality of genomes;
   identifying k-mer sets within the genomic data;
   constructing a k-mer subset tree according to the following process:
      performing iterative pairwise comparisons on the k-mer sets, wherein the iterative pairwise comparisons identify fragments with the most shared k-mers,
      merging the identified fragments into non-leaf nodes of the k-mer subset tree, and
      placing each remaining k-mer into a leaf node of the k-mer subset tree; and
   storing the k-mer subset tree;
   receiving a request for the genomic data; and
   reconstituting at least one genome using non-leaf nodes from a spine of the k-mer subset tree and a corresponding leaf node, wherein the reconstituting does not include decompression of the k-mer sets on loading from storage.

2. The computer-implemented method of claim 1, wherein the iterative pairwise comparisons on the k-mer sets are based on a similarity measure.

3. The computer-implemented method of claim 2, wherein the similarity measure is a Jaccard index.

4. The computer-implemented method of claim 1, wherein the k-mers sets are identified in a single canonical form.

5. The computer-implemented method of claim 4, wherein the canonical form is an alphanumeric form.

6. The computer-implemented method of claim 1, wherein the non-leaf nodes represent subsets of k-mers that do not exist higher up in the k-mer subset tree.

7. The computer-implemented method of claim 1, wherein the leaf nodes represent subsets of k-mers that do not exist higher up in the k-mer subset tree.

8. The computer-implemented method of claim 1, wherein data compression of the k-mers is lossless.

9. The computer-implemented method of claim 1, wherein the k-mer subset tree is constructed based on a known tree selected from the group consisting of: a taxonomic tree and a phylogenetic reference tree.

10. A computer program product for data compression, the computer program product comprising a computer readable storage medium having program instructions embodied therewith, the program instructions executable by a computer to cause the compute to:
   receive, by the computer, genomic data associated with a plurality of genomes;
   identify, by the computer, k-mer sets within the genomic data;
   construct, by the computer, a k-mer subset tree according to the following process:
      perform, by the computer, iterative pairwise comparisons on the k-mer sets, wherein the iterative pairwise comparisons identify fragments with the most shared k-mers,
      merge, by the computer, the identified fragments into non-leaf nodes of the k-mer subset tree, and
      place, by the computer, each remaining k-mer into a leaf node of the k-mer subset tree; and
   store, by the computer, the k-mer subset tree; and
   receive, by the computer, a request for the genomic data; and
   reconstitute, by the computer, at least one genome using non-leaf nodes of a spine of the k-mer subset tree and a corresponding leaf node, wherein the reconstituting does not include decompression of the k-mer sets on loading from storage.

11. The computer program product of claim 10, wherein the iterative pairwise comparisons on the k-mer sets are based on a similarity measure.

12. The computer program product of claim 11, wherein the similarity measure is a Jaccard index.

13. The computer program product of claim 10, wherein the k-mer sets are identified in a single canonical form.

14. The computer program product of claim 10, wherein data compression of the k-mers is lossless.

15. The computer program product of claim 10, wherein the k-mer subset tree is constructed based on a known tree selected from the group consisting of: a taxonomic tree and a phylogenetic reference tree.

16. A system, comprising:
   a processor; and logic integrated with the processor, executable by the processor, or integrated with and executable by the processor, the logic being configured to:

receive genomic data associated with a plurality of genomes;

identify k-mer sets within the genomic data;

construct a k-mer subset tree according to the following process:

perform iterative pairwise comparisons on the k-mer sets, wherein the iterative pairwise comparisons identify fragments with the most shared k-mers, merge the identified fragments into non-leaf nodes of the k-mer subset tree, and place each remaining k-mer into a leaf node of the k-mer subset tree; and store the k-mer subset tree; and receive a request for the genomic data; and reconstitute at least one genome using non-leaf nodes of a spine of the k-mer subset tree and a corresponding leaf node, wherein the reconstituting does not include decompression of the k-mer sets on loading from storage.

17. The system of claim 16, wherein the iterative pairwise comparisons on the k-mer sets are based on a similarity measure.

18. The system of claim 16, wherein data compression of the k-mers is lossless.

* * * * *